(12) United States Patent
Deac et al.

(10) Patent No.: US 6,342,069 B1
(45) Date of Patent: Jan. 29, 2002

(54) SURGICAL INSTRUMENTS UTILIZED TO ASSEMBLE A STENTLESS AUTOLOGOUS TISSUE HEART VALVE

(75) Inventors: Dan Deac, Franklin Park, NJ (US); Radu Deac, Mures (RO)

(73) Assignee: Mures Cardiovascular Research, Inc., St. Paul, MN (US)

( * ) Notice: Subject to any disclaimer, the term of this patent is extended or adjusted under 35 U.S.C. 154(b) by 0 days.

(21) Appl. No.: 09/526,036

(22) Filed: Mar. 15, 2000

Related U.S. Application Data (60) Provisional application No. 60/126,585, filed on Mar. 26, 1999.

(51) Int. Cl.[7] .................................................. A61F 2/24
(52) U.S. Cl. ..................................................... 623/2.1
(58) Field of Search ................................ 623/2.1, 2.11, 623/900, 901, 66; 606/167, 159

(56) References Cited

U.S. PATENT DOCUMENTS

| | | | |
|---|---|---|---|
| 3,898,701 A | 8/1975 | La Russa | 3/1.5 |
| 4,261,342 A | 4/1981 | Aranguren Duo | 128/1 |
| 4,585,453 A | 4/1986 | Martin et al. | 623/2 |
| 4,655,218 A | 4/1987 | Kulik et al. | 128/321 |
| 4,683,883 A | 8/1987 | Martin | 128/303 |
| 4,790,844 A | 12/1988 | Ovil | 623/2 |
| 4,960,424 A | 10/1990 | Grooters | 623/2 |
| 5,163,955 A | 11/1992 | Love et al. | 623/2 |
| 5,197,979 A | 3/1993 | Quintero et al. | 623/2 |
| 5,326,370 A | 7/1994 | Love et al. | 623/2 |
| 5,326,371 A | * 7/1994 | Love et al. | 623/2.1 |
| 5,344,442 A | 9/1994 | Deac | 623/2 |
| 5,370,685 A | * 12/1994 | Stevens | 623/2.11 |
| 5,500,015 A | 3/1996 | Deac | 623/2 |
| 5,697,972 A | 12/1997 | Kim et al. | 623/2 |
| 5,776,187 A | * 7/1998 | Krueger et al. | 623/2.1 |

FOREIGN PATENT DOCUMENTS

EP  WO 91/19465  12/1991  ............. A61F/2/24

* cited by examiner

*Primary Examiner*—Kevin Truong
(74) *Attorney, Agent, or Firm*—Kinney & Lange P.A.

(57) ABSTRACT

A valve assembly kit consisting of a plurality of specialized surgical instruments used for a reproducible, standardized technique to rapidly assemble a heart valve in the operating room from autologous tissue. The specialized surgical instruments of the valve assembly kit of the present invention are used to tailor, process (preserve) and assemble an autologous pericardium heart valve in relation with the anatomical configuration of the left ventricle and mitral annulus. The valve assembly kit generally consists of a tissue processing tray that supports the following specialized surgical instruments/devices: a tissue cutting device, an obturator with a removable handle, a valve assembly tray, and a universal stentless valve holder. These specialized surgical instruments will be used to rapidly (15–20 min.) assemble a heart valve in the operating room, at the time of the mitral valve replacement, from autologous tissue.

24 Claims, 12 Drawing Sheets

| DIMENSIONS OF THE CUTTING BLADE (mm) | | | | | | | | | |
|---|---|---|---|---|---|---|---|---|---|
| DIAMETER M. RING | CIRCUMFERENCE M. RING - [C] | L [C/2] | B1 [C/2] | B2 [0.6×C] | B3 [0.48×C] | E [0.1×C] | F [0.2×L] | G [(B2-B1)/2] | H √G2+L2 |
| 28 | 90 | 45 | 45 | 54 | 43.2 | 9 | 9 | 4.5 | 45.22 |
| 30 | 95 | 47 | 47 | 57 | 45.6 | 9.5 | 9.5 | 5 | 47.27 |
| 31 | 100 | 50 | 50 | 60 | 48 | 10 | 10 | 5 | 50.25 |
| 33 | 105 | 52 | 52 | 63 | 50.4 | 10.5 | 10.4 | 5.5 | 52.29 |
| 35 | 110 | 55 | 55 | 66 | 52.8 | 11 | 11 | 5.5 | 55.27 |

OBTURATOR DIMENSIONS (mm)

| OBTURATOR SIZE | CIRCUMFERENCE | A LONG AXIS | F SHORT AXIS | B 0.375×A | C A+10 | D A-4 | E F+10 | G F-4 |
|---|---|---|---|---|---|---|---|---|
| 28 | 90 | 33 | 24.00 | 12.375 | 43 | 29 | 34.00 | 20.00 |
| 30 | 95 | 35 | 25.19 | 13.125 | 45 | 31 | 35.19 | 21.19 |
| 31 | 100 | 36 | 27.44 | 13.500 | 46 | 32 | 37.44 | 23.44 |
| 33 | 105 | 38 | 28.63 | 14.250 | 48 | 34 | 38.63 | 24.63 |
| 35 | 110 | 40 | 29.73 | 15.000 | 50 | 36 | 39.73 | 25.73 |

SURGICAL INSTRUMENTS UTILIZED TO ASSEMBLE A STENTLESS AUTOLOGOUS TISSUE HEART VALVE

CROSS-REFERENCE TO RELATED APPLICATION

This application claims priority from U.S. Provisional Patent Application Ser. No. 60/126,585 filed on Mar. 26, 1999, for "Surgical Instruments Utilized To Assemble A Stentless Autologous Tissue Heart Valve" by Dan Deac and Radu Deac.

BACKGROUND OF THE INVENTION

The present invention relates generally to cardiac valve replacement in heart surgery, and particularly to a valve assembly kit consisting of a plurality of specialized surgical instruments used for a reproducible, standardized technique to rapidly assemble a heart valve in the operating room from autologous tissue.

In recent years, cardiac valve replacement surgery has become a common procedure. Many cardiac valves are now replaced with valves constructed from autologous tissue. "Autologous tissue" is any tissue harvested from the human or animal subject such as heart valves, pericardium, arteries, veins, organ capsules and the like, which is intended to be reimplanted in the same subject. The mitral valve is one such valve that has been constructed from autologous tissue.

The mitral valve is generally a thin continuous, flexible membrane, strengthened by collagen fibers, surrounding the left atrio-ventricular ring having two indentations or commissures dividing it into two principal trapezoidal leaflets of unequal size. The details of the mitral valve anatomy are described in U. S. Pat. Nos. 5,344,442 and 5,500,015 to Radu Deac, which are incorporated herein by reference and assigned to the same assignee as the present application. Under normal conditions, the mitral valve is exposed to the greatest pressure and stress during the cardiac cycle. However, in comparison with aortic, tricuspid and pulmonary valve replacement procedures, mitral valve replacement procedures have exhibited the poorest results in terms of morbidity and mortality.

The ideal valve substitute should be designed to reproduce as accurately as possible the normal flow pattern in the left side of the heart. The valve should have a large orifice, unrestrictive to a central free flow. It should operate at a low opening pressure without gradients across the valve, and be compatible with high outputs at exercise. The valve should exhibit rapid opening and closure throughout its entire range of pressures without regurgitant flow and without obstruction to the left ventricular output flow. The ideal valve substitute should be attached to the papillary muscles in such a manner as to maintain the valvular-papillary muscle continuity with a minimum of stress to thereby preserve the mechanics and contractural movement of the left ventricle. The valve should provide a uniform distribution of forces and stresses and avoid compressive, tensile or flexure stress during operation. The ideal valve should be constructed entirely of flexible tissue, without mechanical stents and the like. It should exhibit a long life, be durable, resistant to wear and resistant to degeneration, calcification and infection. It should provide normal heart sounds, without noise. It should produce no thrombo-embolic complications, and avoid trauma to blood elements. It should function normally as the left ventricle changes in size. The ideal valve should be easy and reliable to produce and implant.

The prior art replacement heart valves and techniques for forming such valves do not meet these criteria because of the difficulties involved in harvesting, forming, and implanting a suitable valve in the operating room. Thus, there is a need for a sterile valve assembly kit that can rapidly assemble a heart valve in the operating room, at the time of the mitral valve replacement, from autologous tissue.

BRIEF SUMMARY OF THE INVENTION

The present invention is a valve assembly kit consisting of a plurality of specialized surgical instruments used for a reproducible, standardized technique to rapidly assemble a heart valve in the operating room from autologous tissue. The specialized surgical instruments of the valve assembly kit of the present invention are used to tailor, process (preserve) and assemble an autologous pericardium heart valve in relation with the anatomical configuration of the left ventricle and mitral annulus. The valve assembly kit generally consists of a tissue processing tray that supports the following specialized surgical instruments/devices: a tissue cutting device, an obturator with a removable handle, a valve assembly tray, and a universal stentless valve holder. These specialized surgical instruments will be used to rapidly (15–20 min.) assemble a heart valve in the operating room, at the time of the mitral valve replacement, from autologous tissue.

DETAILED DESCRIPTION

The present invention is a valve assembly kit consisting of a plurality of specialized surgical instruments used for a reproducible, standardized technique to rapidly assemble a heart valve in the operating room from autologous tissue. The specialized surgical instruments of the valve assembly kit of the present invention are used to tailor, process (preserve) and assemble an autologous pericardium heart valve in relation with the anatomical configuration of the left ventricle (mitral annulus—papillary muscle length) and mitral annulus (circumference/perimeter). The specialized surgical instruments of the valve assembly kit will be used to rapidly (15–20 min.) assemble a heart valve in the operating room, at the time of the mitral valve replacement, from autologous tissue (pericardium).

After the heart and the pericardium are exposed during valve replacement surgery, the surgeon will excise a rectangular fragment of pericardium (preferably approximately 100 mm by 50 mm) from the antero-lateral region of the pericardial sac. A preferred method of harvesting autologous tissue is known in the art and described in U.S. Pat. Nos. 5,344,442 and 5,500,015 to Radu Deac, which are incorporated herein by reference and assigned to the same assignee as the present application. The quality, thickness, orientation of fibers and strength may determine the outcome of the medical device. Specifically in the case of pericardium, mapping of these characteristics facilitate proper tissue selection. Detailed mapping of mechanical and biological characteristics of whole pericardia has revealed that the areas overlying the anterior ventricular surface were designated as "areas of choice" for tissue selection.

Before the pericardial tissue fragment can be processed with the inventive valve assembly kit, the pericardial fragment must be properly cleaned and its quality verified. The pericardial fragment will be cleaned of any fatty deposits and carefully inspected for irregularities in tissue continuity and thickness. After proper cleaning and quality control, the pericardial fragment is ready for the next step.

Figure 1:
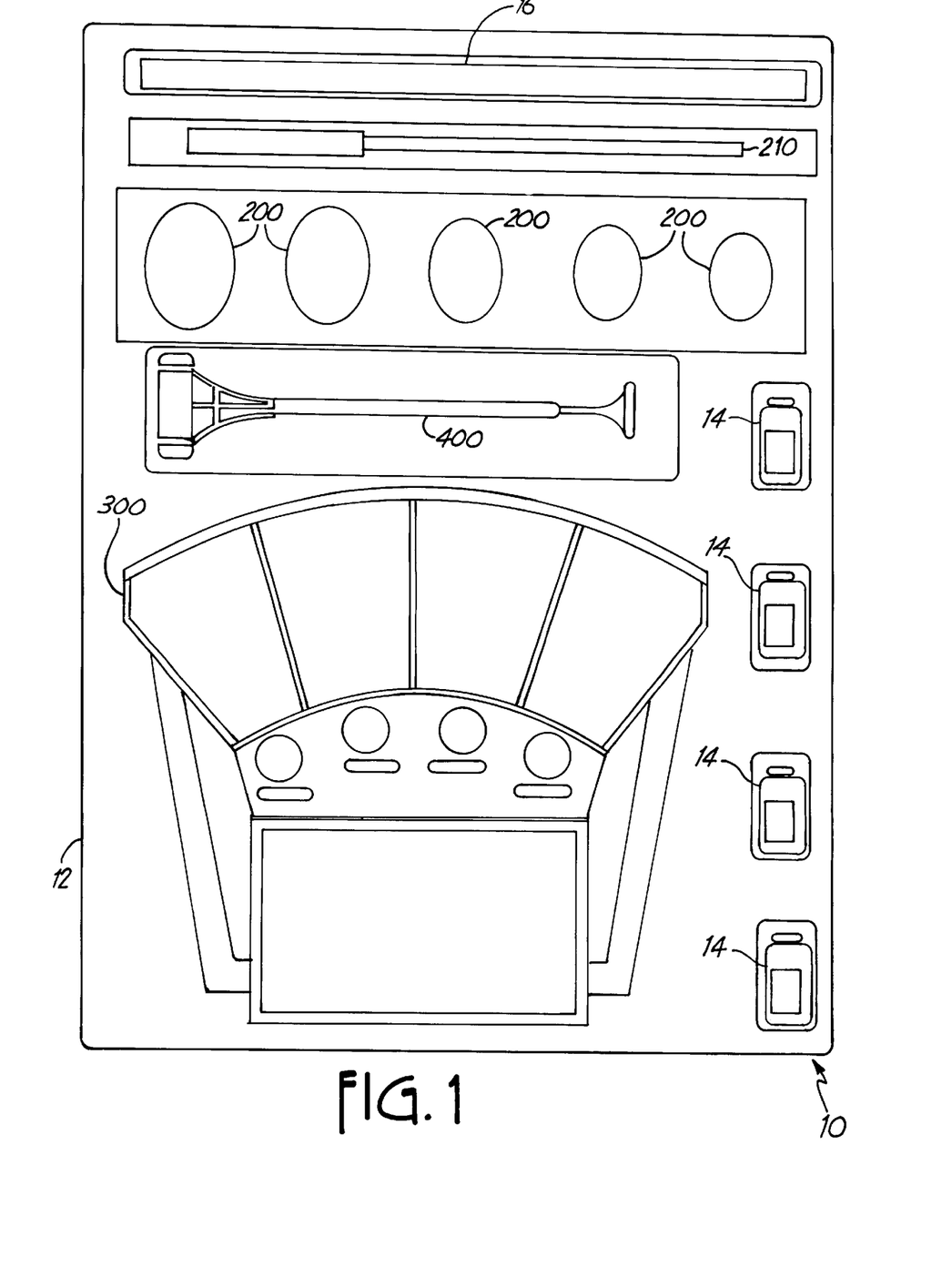
FIG. 1 is a top view of a valve assembly kit of the present invention that generally includes a tissue cutting device (shown in FIG. 2), an obturator with a removable handle, a valve assembly tray, and a universal stentless valve holder.

An overview of the heart valve construction using the valve assembly kit of the present invention is now provided. The surgeon will open a sterile Valve Assemble Kit 10 that is shown in FIG. 1. The valve assembly kit 10 generally consists of a tissue processing tray 12 that supports the following specialized surgical instruments/devices: a tissue cutting device 100 (shown in FIG. 2), an obturator 200 with a removable handle 210, a valve assembly tray 300, and a universal stentless valve holder 400. The tissue processing tray 12 also supports a measurement ruler 16 for any measurements the surgeon must make during the procedure. A detailed analysis of the role of each of these specialized surgical instruments/devices in the valve assembly kit 10 follows the overview of the heart valve construction.

After opening the valve assembly kit 10, the surgeon places solution bottles 14 in the corresponding, labeled bottle holders on the tissue processing tray 12. After the solution bottles 14 are correctly placed on the tissue processing tray 12, each solution will be carefully poured into the corresponding basin. By following the instructions provided with the valve assembly kit 10, the tissue fragment will be rinsed and chemically processed.

After rinsing and chemically processing the tissue fragment, the surgeon will connect a removable universal handle 210 to one of a plurality of various sized obturators 200, and measure the inner circumference of the mitral annulus. Several measurements are necessary, with different sized obturators 200, to precisely assess the circumference of the mitral annulus. After the correct obturator 200 is selected, the surgeon will read the code number on the obturator 200, and choose the matching cutting block with the same code number. Having the correct cutting block, the surgeon can use the tissue cutting device 100 to excise the two tissue fragments, necessary to assemble the pericardial heart valve. Each obturator 200 matches a standardized, size specific cutting block that will produce a heart valve, identical in circumference with the obturator 200.

In the next step, the surgeon will construct the heart valve on the valve assembly tray 300 using the two tissue fragments obtained in the previous step. In the final step, the surgeon will place the assembled valve on the universal stentless valve holder 400, and prepare for the implantation in the mitral position. During the entire process, the pericardium tissue will be rinsed in isotonic saline solution to preserve its moisture. The pericardium must be handled with care to avoid any mechanical damage. During implantation, the surgeon will manipulate the valve using the valve holder 400 to avoid any mechanical damage.

The Tissue Cutting Device 100

The tissue cutting device 100 is utilized to tailor the pericardium to a size specific shape that will correspond with the dimensions previously measured with the obturator 200. The tissue cutting device 100 will be used as a cutting tool to process the excised pericardium, and to obtain size and shape specific components necessary to manufacture the tissue heart valve.

Figure 2:
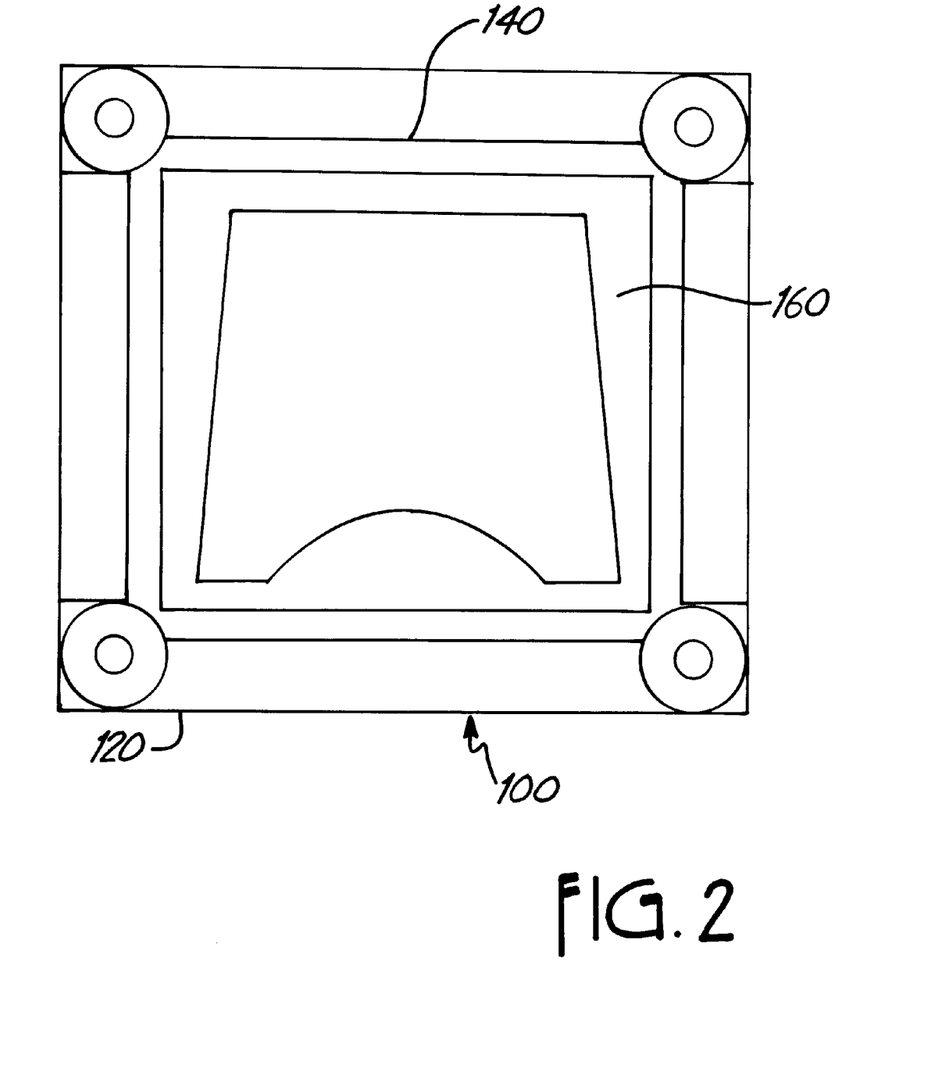
FIG. 2 is a top view of a tissue cutting device of a valve assembly kit of the present invention including a base unit, a guiding frame, and a cutting block.
Figure 6:
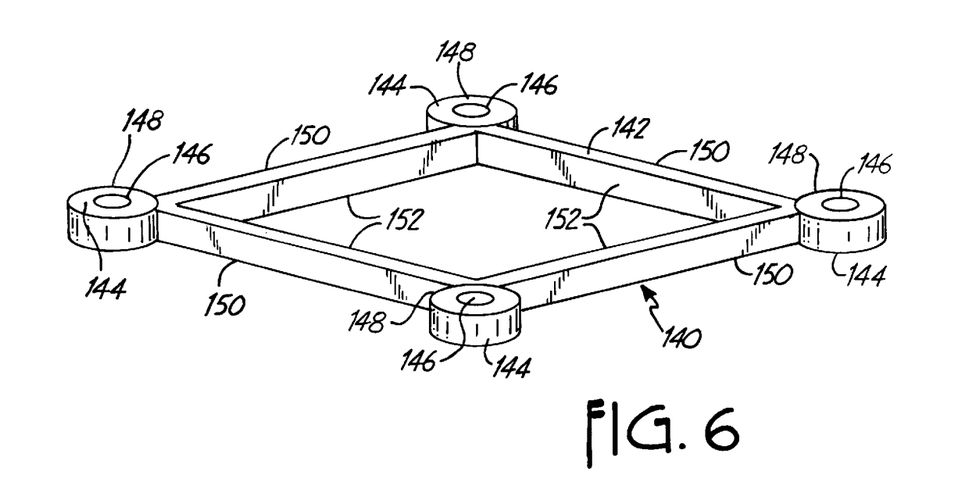
FIG. 6 is a three-dimensional perspective view of a guiding frame of a tissue cutting device of the present invention.
Figure 7:
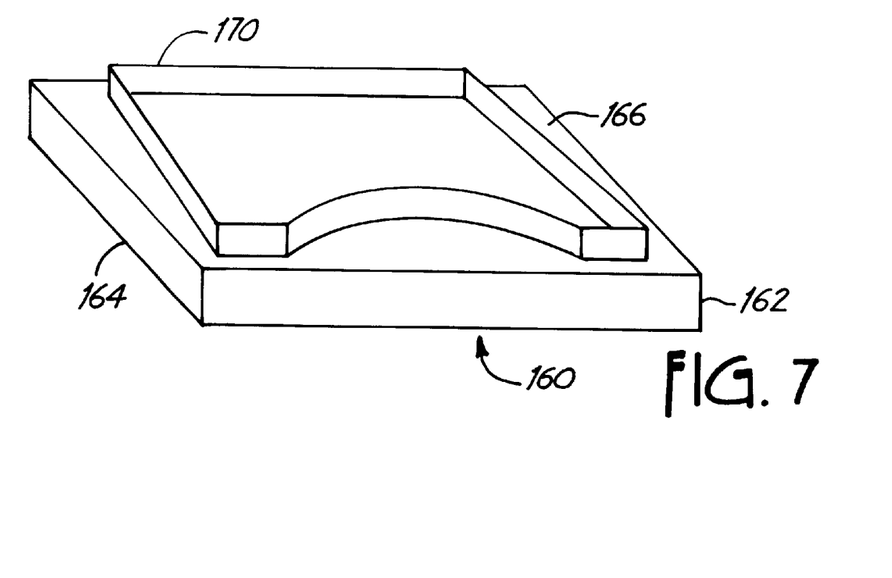
FIG. 7 is a three-dimensional perspective view of a cutting block of a tissue cutting device of the present invention.
Figure 8:
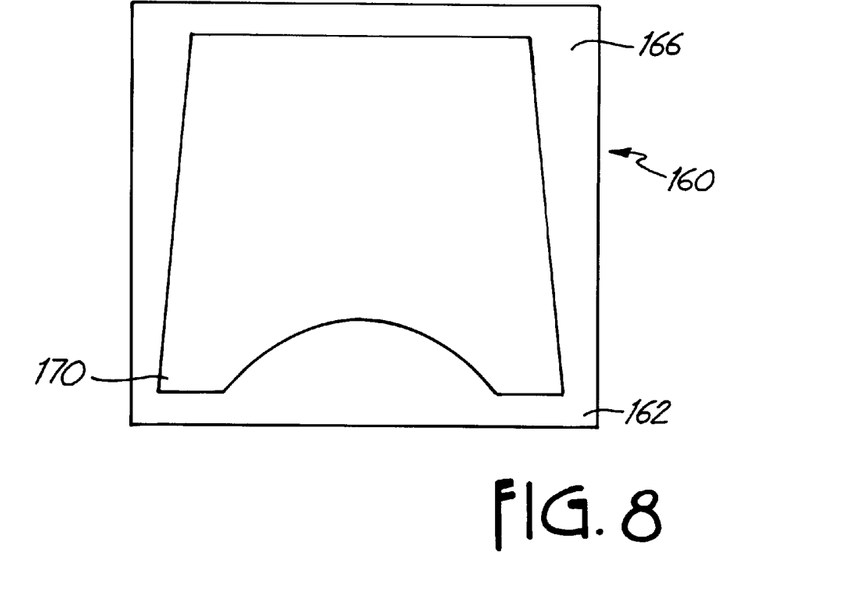
FIG. 8 is a top view of a cutting block of a tissue cutting device of the present invention.

As shown in FIG. 2, the tissue cutting device 100 consists of three components: a base unit 120 (FIGS. 3, 4); a guiding frame 140 (FIGS. 5, 6); and a cutting block 160 (FIGS. 7, 8). The preferred embodiments for the tissue cutting device 100 are illustrated in FIGS. 2–8. All parts of the tissue cutting device 100 are made out of a transparent biocompatible plastic material to provide increased visibility that is necessary for adequate manipulation of the tissue (pericardium). Each component of the tissue cutting device 100 has a specific role in the mechanism of action of the tissue cutting device 100.

Figure 3:
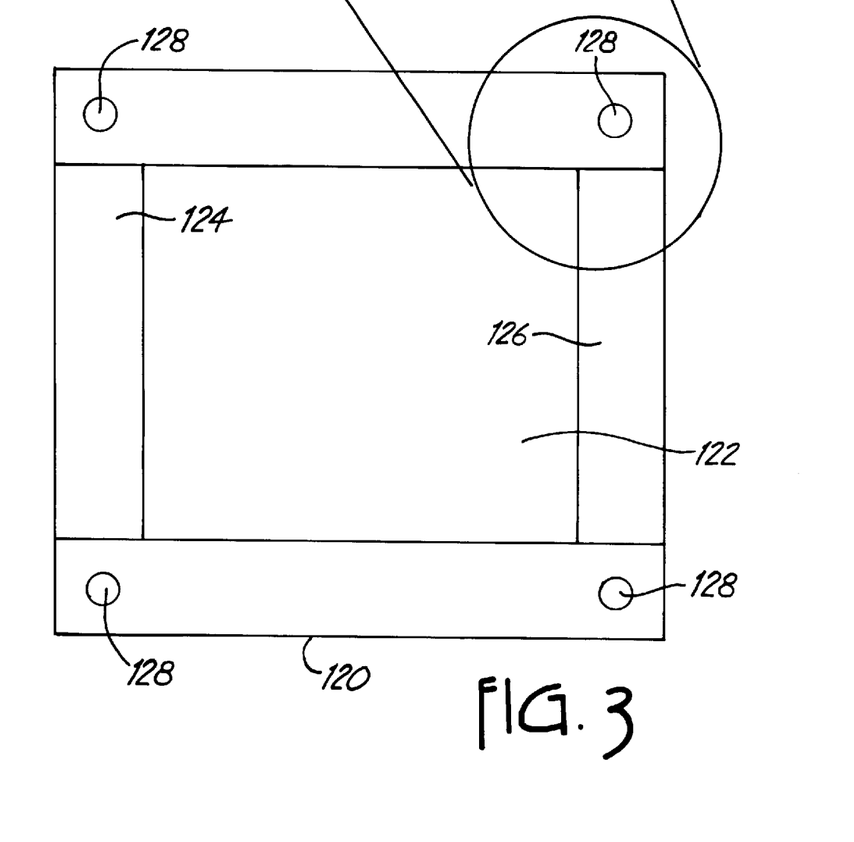
FIG. 3 is a top view of a base unit of a tissue cutting device of the present invention.

As shown in FIG. 3, the base unit 120 has a rectangular shape, preferably dimensioned to be 106 mm by 95 mm by 10 mm. The base unit 120 is composed of a transparent biocompatible plastic and has four guide pegs 128 also composed of a transparent biocompatible plastic. The role of the base unit 120 is to provide a hard horizontal surface used to process the pericardium.

Figure 4:
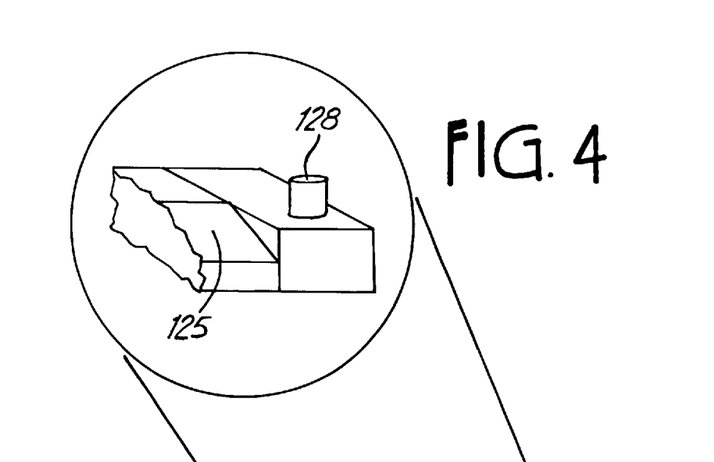
FIG. 4 is a fragmentary three-dimensional sectional view of a base unit of a tissue cutting device of the present invention.

The base unit 120 consists of a horizontal rectangular surface 122 preferably dimensioned to be 76 mm by 62.70 mm, two inclined rectangular surfaces 124, 126, and four guide pegs 128. Each guide peg 128 has a cylindrical shape a preferred length of 11 mm and a preferred diameter of 6 mm. The function of the 10 guide pegs 128 is to guide the placement of the guiding frame 140 over base unit 120 of the tissue cutting device 100. The inclined rectangular surfaces 124 and 126 have an inclined surface 125 of approximately 30°–40° from horizontal to facilitate the manipulation of the tissue during the cutting process. The preferred dimensions of inclined surface 125 are 63 mm by 15.8 mm by 10 mm, with a thickness of 5 mm. FIG. 4 shows a three dimensional sectional view of a fragment of the inclined rectangular surfaces 124, 126.

Figure 5:
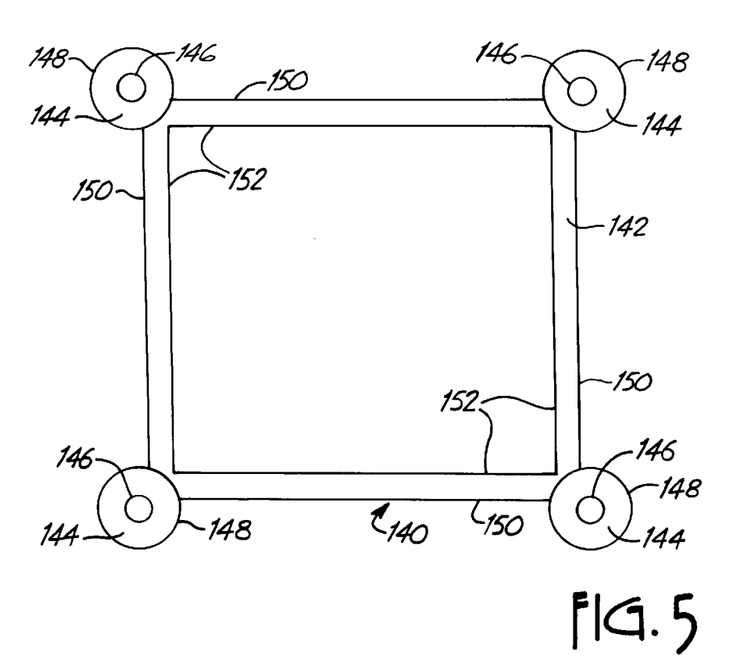
FIG. 5 is a top view of a guiding frame of a tissue cutting device of the present invention.

As shown in FIG. 5, the guiding frame 140 of the tissue cutting device 100 consists of a rectangular frame 142 and four guide rings 144 located in each corner of the rectangular frame 142. The function of the rectangular frame 142 is to precisely guide the cutting block 160 against the horizontal rectangular surface 122 of the base unit 120, and to secure the tissue fragment on the base unit 120. The preferred dimensions of an outer perimeter 150 of the rectangular frame 142 are 86 mm by 75 mm by 5 mm, with a thickness of 5 mm. An inner perimeter 152 of the rectangular frame has preferred dimensions of 76 mm by 65 mm by 5 mm. The guide rings 144 have an inner diameter 146 of 6 mm and an outer diameter 148 of 16 mm. The role of the guide rings 144 is to direction the placement of the guiding frame 140 on the base unit 120 by matching the four guide pegs 128. FIG. 6 is a three-dimensional representation of the guiding frame 140.

As shown in FIGS. 7 and 8, the cutting block 160 consists of a rectangular block 162 and a cutting blade 170, having a specific size and shape. The cutting block 160 is used in a similar manner to a cookie cutter, to cut out the tissue fragment previously placed on the base unit 120 and kept in place by the guiding frame 140. The cutting block 160 is aligned by the guiding frame 140 to precisely lie over the tissue fragment and cut off the desired shape. Because the cutting block 160 is made out of a transparent plastic material, the surgeon will be able to visually monitor the cutting process and make any necessary adjustments to the tissue fragment.

The rectangular block 162 is preferably composed of plastic and has the preferred dimensions of 76 mm by 65 mm by 10 mm. An upper surface 164 of the rectangular block 162 is plane and will be used by the surgeon to apply the necessary pressure to cut the tissue fragment. A lower surface 166 of the rectangular block 162 contains a cutting blade 170 embedded in the plastic rectangular block 162. The shape of the cutting blade 170 has the same outline as the desired shape of the tissue fragment, necessary for a specific valve size. The cutting blade 170 is razor-sharpened to about 100–300 Angstrom, and made out of a single piece of surgical steel, so that only a small amount of pressure is required to cut out the desired tissue fragment. The sharpness of the cutting blade 170 is crucial, since the surgeon must cut the tissue fragment with one strike. Multiple attempts to cut the same tissue fragment will damage the edges of the biologic material. The cutting blade 170 is perpendicular to the horizontal surface of the cutting block 160 and to the horizontal rectangular surface 122 of the base unit 120 of the tissue cutting device 100. The cutting blade 170 is molded into the plastic rectangular block 162 and extends approximately 2–3 mm above the lower surface 166 of the cutting block 160. FIG. 7 shows the three dimensional configuration of the cutting block 160 and the cutting blade 170.

The valve assembly kit 10 of the present invention provides five cutting blocks 160, each having a specific code number (i.e., 28, 30, 31,33 and 35) on the top surface that corresponds to a specific obturator size. After the surgeon measures the mitral orificial perimeter/circumference (C) with the obturators 200, the surgeon will select the correct cutting block 160 that will match the obturator code number. Having the correct cutting block 160, the surgeon can use the tissue cutting device 100 to excise the two tissue fragments necessary to assemble the pericardial heart valve.

Figure 9:
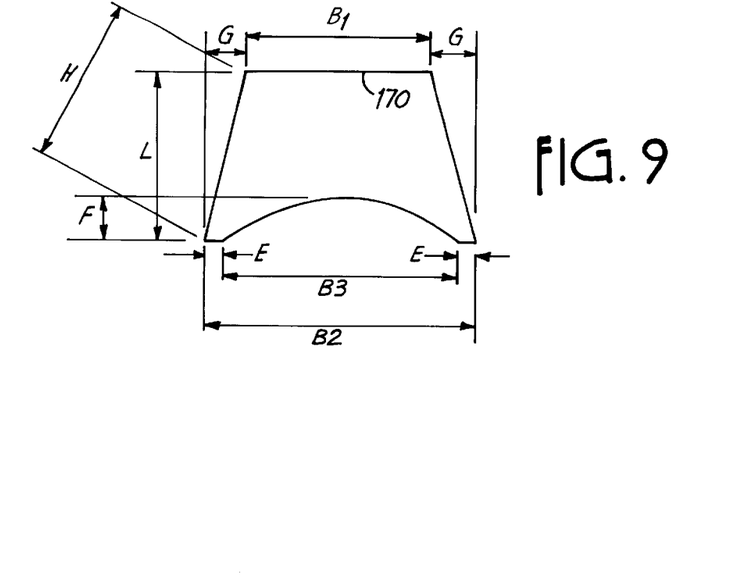
FIG. 9 shows the contour of a cutting blade of a cutting block of a tissue cutting device of the present invention and explains the abbreviations used in FIG. 10.
Figure 10:
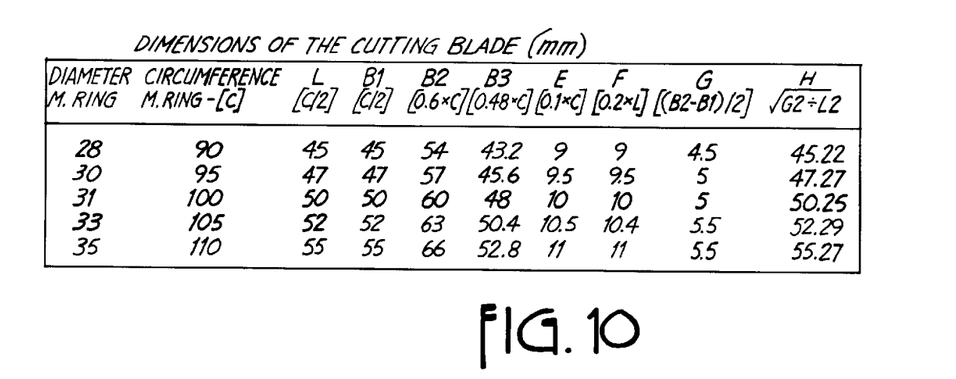
FIG. 10 lists the dimensions of each side of the five cutting blades included with a tissue cutting device of a valve assembly kit of the present invention.

The dimensions of each side of the five cutting blades 170 are displayed in FIGS. 9 and 10. FIG. 9 shows the contour of the cutting blade 170 and explains the abbreviations used in FIG. 10. In FIG. 10, the first column represents the code number for the five dimensions that corresponds with the diameter in millimeters of the mitral valve annulus for a specific size. The second column represents the circumference (C) in millimeters of the mitral valve annulus for a specific size. The circumference (C) will be used to calculate all the dimensions of the cutting blade.

The Obturator 200 With The Removable Handle 210

Figure 11:
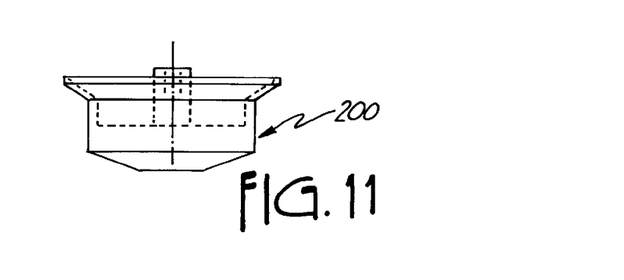
FIG. 11 is a side view of an obturator of a valve assembly kit of the present invention.

The obturator 200 is shown in FIG. 11. The purpose of the obturator 200 with the removable handle 210 is to accurately measure the circumference of the mitral annulus, necessary for the correct selection of the tissue heart valve size. As shown in FIG. 1, the tissue processing tray 12 holds several obturators 200 with different sizes and one universal detachable handle 210.

Figure 12:
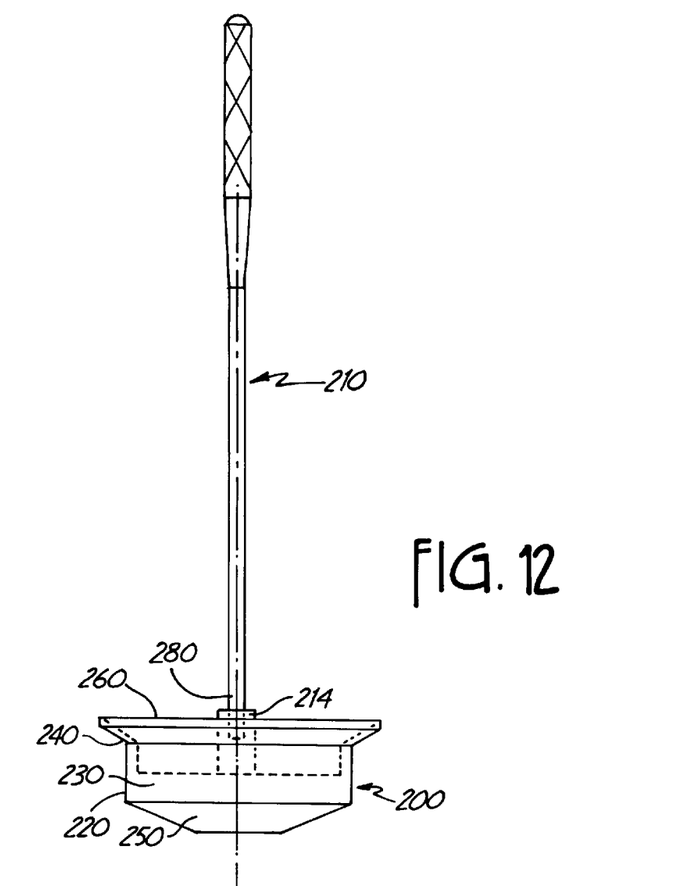
FIG. 12 is a side view of an obturator with a removable handle of a valve assembly kit of the present invention.
Figure 13:
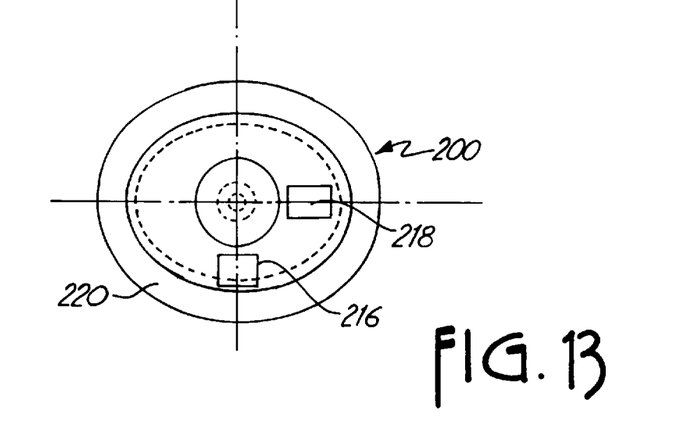
FIG. 13 is a top view of an obturator with a removable handle of a valve assembly kit of the present invention.

As shown in FIG. 12, the surgeon will assemble the obturator 200 with the removable handle 210 by screwing a threaded portion 280 of the removable handle 210 into the threaded attachment unit 214 of the obturator 200. The obturator will then be introduced into the mitral annulus to evaluate its orificial circumference (perimeter). This measurement will be performed several times, with different obturators 200 to determine the closest fit. Once the correct obturator 200 is chosen, the surgeon will read a code number 216 printed on the superior part of the obturator 200 (FIG. 13), which will correspond with a specific kit number used in the manufacture of the correct tissue heart valve. The obturator 200 will also have engraved the orificial circumference value 218 for that particular size.

The obturator body 220 will be constructed from a transparent biocompatible plastic material to facilitate the correct orientation and placement in the mitral annulus. In a transverse cross section the obturator 200 has an elliptical shape which corresponds with the anatomical configuration of the mitral annulus. From a lateral view, the obturator 200 has three regions, each of them having a precise role in the function of the instrument. A middle region 230 will be in close contact with the mitral annulus surface and will evaluate the dimension of the ring. The middle region 230 is the most important region of the obturator 200, that will provide the necessary information regarding the perimeter of the mitral annulus. A top region 240 of the obturator 200, is located above the middle region 230, and will lie on the supra annular area to prevent further progression of the obturator 200 into the mitral orifice. A bottom region 250 of the obturator 200 has a conical shape, to prevent any damage to the anatomical structures that will come in contact with the instrument. An upper surface 260 of the obturator 200 supports the threaded attachment unit 214 located in the center of the ellipse. The threaded attachment unit 214 represents the coupling point between the obturator 200 and the threaded portion 280 of the removable handle 210.

Figure 14:
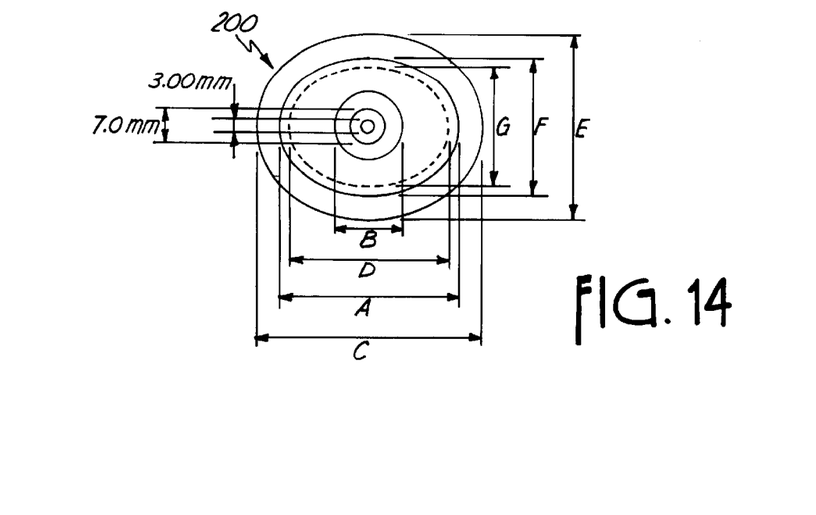
FIG. 14 shows a graphical representation of an obturator of a valve assembly kit of the present invention and explains the abbreviations used in FIG. 15.
Figure 15:
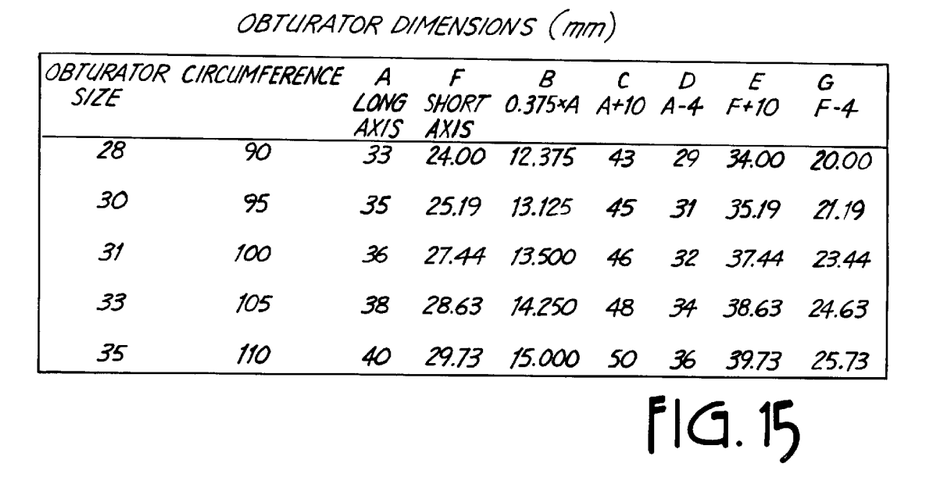
FIG. 15 lists the dimensions of five obturators included with the valve assembly kit of the present invention.
Figure 16:
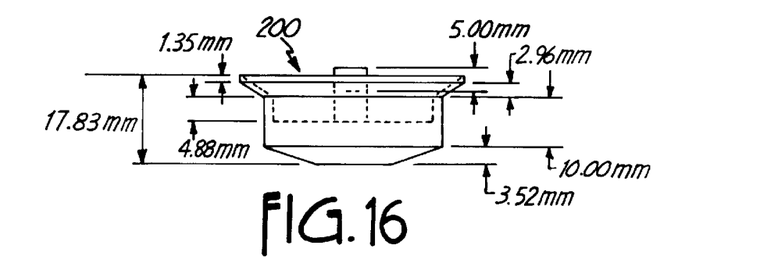
FIG. 16 is a side view of an obturator showing specific dimensions of the obturators included with the valve assembly kit of the present invention.

The valve assembly kit 10 provides a set of five obturators 200 with varying dimensions. The dimensions of five obturators 200 are displayed in FIGS. 14, 15 and 16. FIG. 14 shows a graphical representation of the obturator 200 with explanations of the abbreviations used in FIG. 15. All five obturators 200 have the same length, and the rest of the dimensions are calculated in relationship with the long axis (A) and short axis (F) of the ellipse. FIG. 16 shows specific dimensions of the obturator 200.

Figure 17:
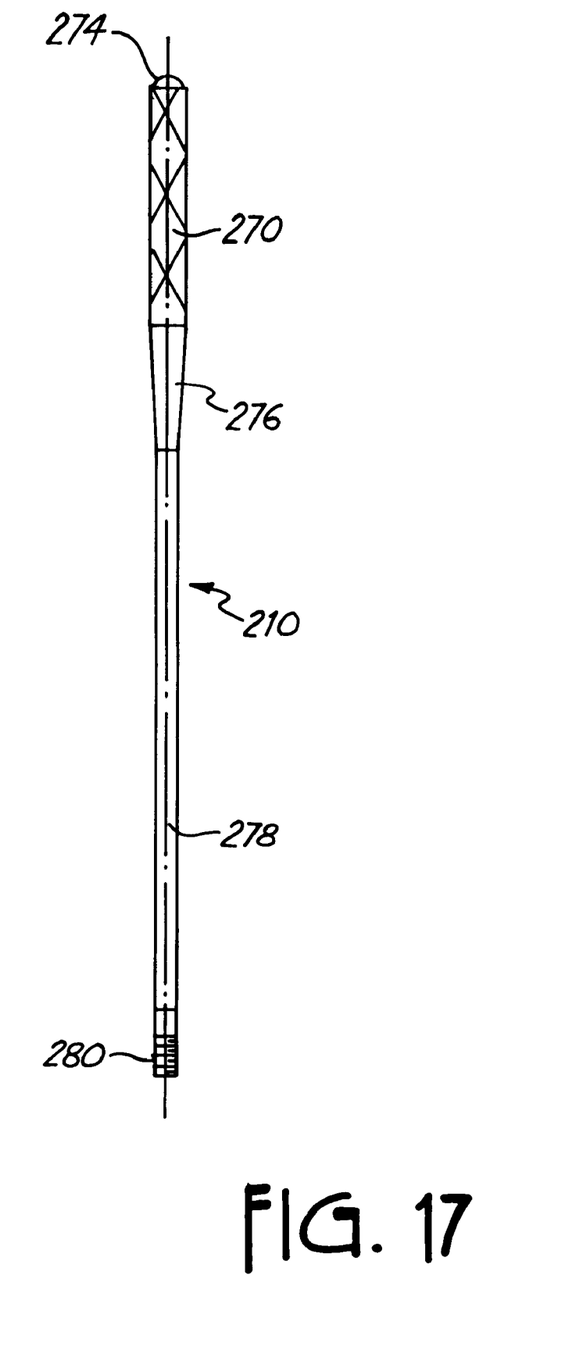
FIG. 17 is a side view of a removable handle of a valve assembly kit of the present invention.

As shown in FIG. 17, the removable handle 210 is composed of four major segments. An gripping segment 270 is used to hold and manipulate the removable handle 210. The gripping segment 270 is a rigid cylindrical segment made out of opaque biocompatible plastic material or a light metal. The gripping segment 270 has preferred dimensions of 28.78 mm in length and 5 mm in diameter.

A spherical end cap segment 274 is attached to an upper extremity of the gripping segment 270. The spherical end cap segment 274 having a preferred radius of 2.82 mm and a preferred length of 1.47 mm. The spherical end cap segment 274 protects the surgeon's hand during manipulation of the obturator 200 in the operatory field.

A transition segment 276 is a transitional element between the upper segment 270 and a lower cylindrical segment 278. The transition segment 276 has a conical shape and is made of the same material as the upper segment 270. The transition segment 276 has a preferred length of approximately 15.00 mm and will have identical preferred diameters as the adjacent segments the upper segment 270 and the lower cylindrical segment 278.

The lower cylindrical segment 278 is the connecting element between the removable handle 210 and the obturator 200 and is made out of a malleable material (plastic or metal wire) that can be deformed by the surgeon to make an angle ranging from 10 to 50 degrees. This angled handle is necessary for the proper manipulation and measurement of the mitral annulus. A lower end of lower cylindrical segment 278 has the threaded portion 280 that will couple the handle with the obturator 200. The threaded portion 280 of the lower cylindrical segment 278 has a preferred length of 5 mm. The lower cylindrical segment 278 has a preferred length of approximately 76 mm, and a preferred diameter of 3.00 mm.

The Valve Assembly Tray 300

Figure 18:
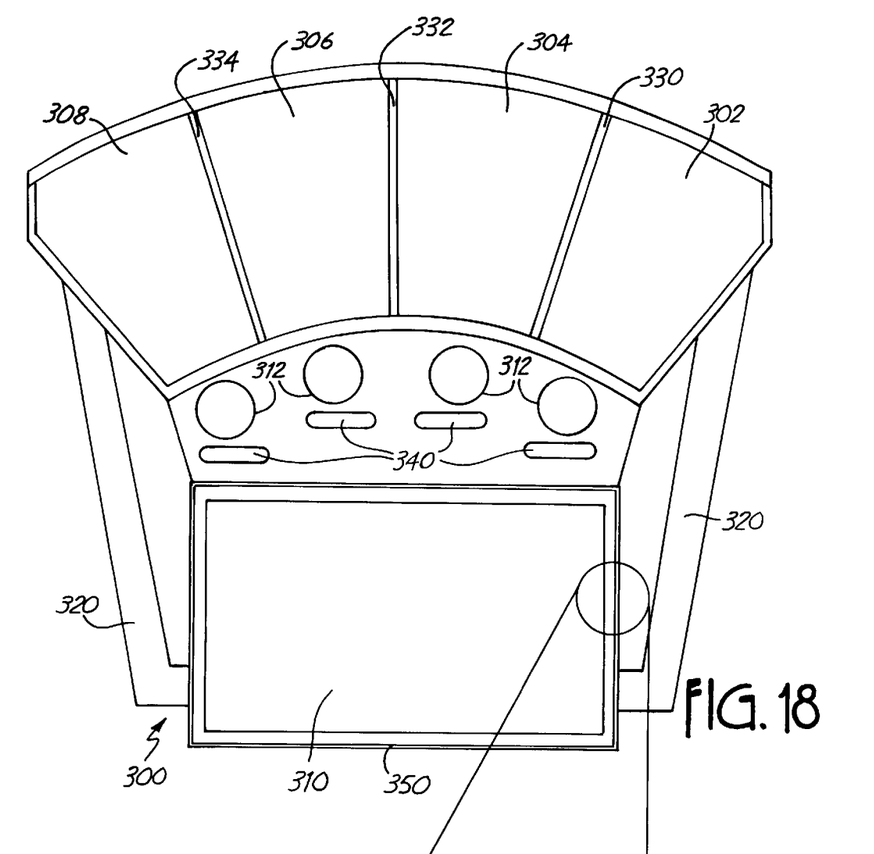
FIG. 18 is a top view of a valve assembly tray of a valve assembly kit of the present invention.

The valve assembly tray 300 will be used to mechanically and chemically process the autologous pericardium and assemble the tissue heart valve. As shown in FIG. 18, the valve assembly tray 300 consists of four basins 302, 304, 306 and 308; a plane rectangular surface 310; four solution bottle stands 312; and two handles 320.

The basins 302, 304, 306 and 308 will be used to rinse, chemically process and store the tissue fragments (pericardium) after prelevation and during the entire manipulation process. The volume capacity of each basin is between 200 ml–400 ml. The basins 302, 304, 306 and 308 have preferred dimensions of approximately 50 mm by 40 mm by 30 mm. The outer walls of the basins 302,304, 306 and 308 have a preferred thickness of 5 mm and the lateral walls 330, 332 and 334 that divide the basins 302, 304, 306 and 308 have a preferred thickness of 4 mm. The basins 302, 304, 306 and 308 are contoured to be large enough to permit the manipulation of the tissue fragments with a traumatic forceps. Each basin 302, 304, 306 and 308 will be filled with a specific solution, provided with the valve assembly kit 10, that will match labels 340 printed below each solution bottle stand 312.

The solution bottle stands 312 are cylindrical depressions that match the preferred outer diameter (30 mm) of the solution bottles 14, and represent a storage place for the solution bottles 14 after the solutions have been used. The solution bottle stands 312 have a depth of approximately 10 mm and are preferably deep enough to keep the solution bottles 14 in place. Having the label 340 below each solution bottle stand 312, the surgeon can follow the correct sequence of chemical processing. Each label 340 has the name of a specific solution that will correspond with the bottle label, in order to avoid any misunderstanding or misplacement. The label 340 has preferred dimensions of approximately 30 mm by 5 mm.

Figure 19:
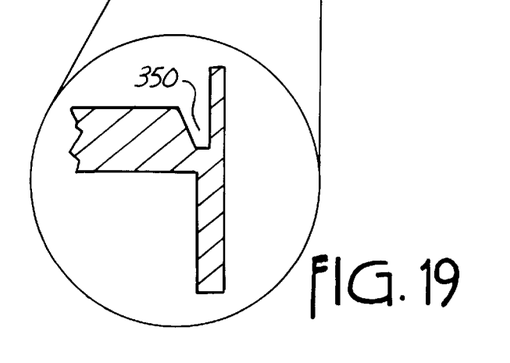
FIG. 19 is an enlarged cross section view of the grooved channel surrounding the rectangular surface of the valve assembly tray of the valve assembly kit of the present invention.

The plane rectangular surface 310 is used for the mechanical manipulation of the tissue fragments (autologous pericardium) during the entire process of tissue heart valve assembly. The approximate dimensions of the rectangular surface 310 are 150 mm by 100 mm by 25 mm. Around this rectangle, A grooved channel 350, having a preferred thickness of 2 mm and a preferred depth of 2–3 mm, surrounds the rectangular surface 310. The grooved channel 350 is designed to drain any fluids that will tend to collect on the rectangular surface 310 during the manipulation of the tissue fragments (autologous pericardium). The grooved channel 350 is trapezoidal in shape and located along a perimeter edge of the plane rectangular surface 310. The grooved channel 350 surrounding the rectangular surface 310 of the valve assembly tray 300 is illustrated in the enlarged cross section in FIG. 19.

After the rectangular piece of pericardium has been harvested, the tissue is rinsed in saline and cleaned from any fatty deposits or other irregularities. After this preliminary step the tissue is chemically processed by successively dipping the pericardium in the four basins 302, 304, 306 and 308, each basin having a different solution with a specific immersion time.

Each side of the valve assembly tray 300 has a handle 320 for easy handling by the surgical personnel. The preferred dimensions of the handles are approximately 140 mm by 10 mm by 10 mm.

The Universal Stentless Valve Holder 400

Figure 20:
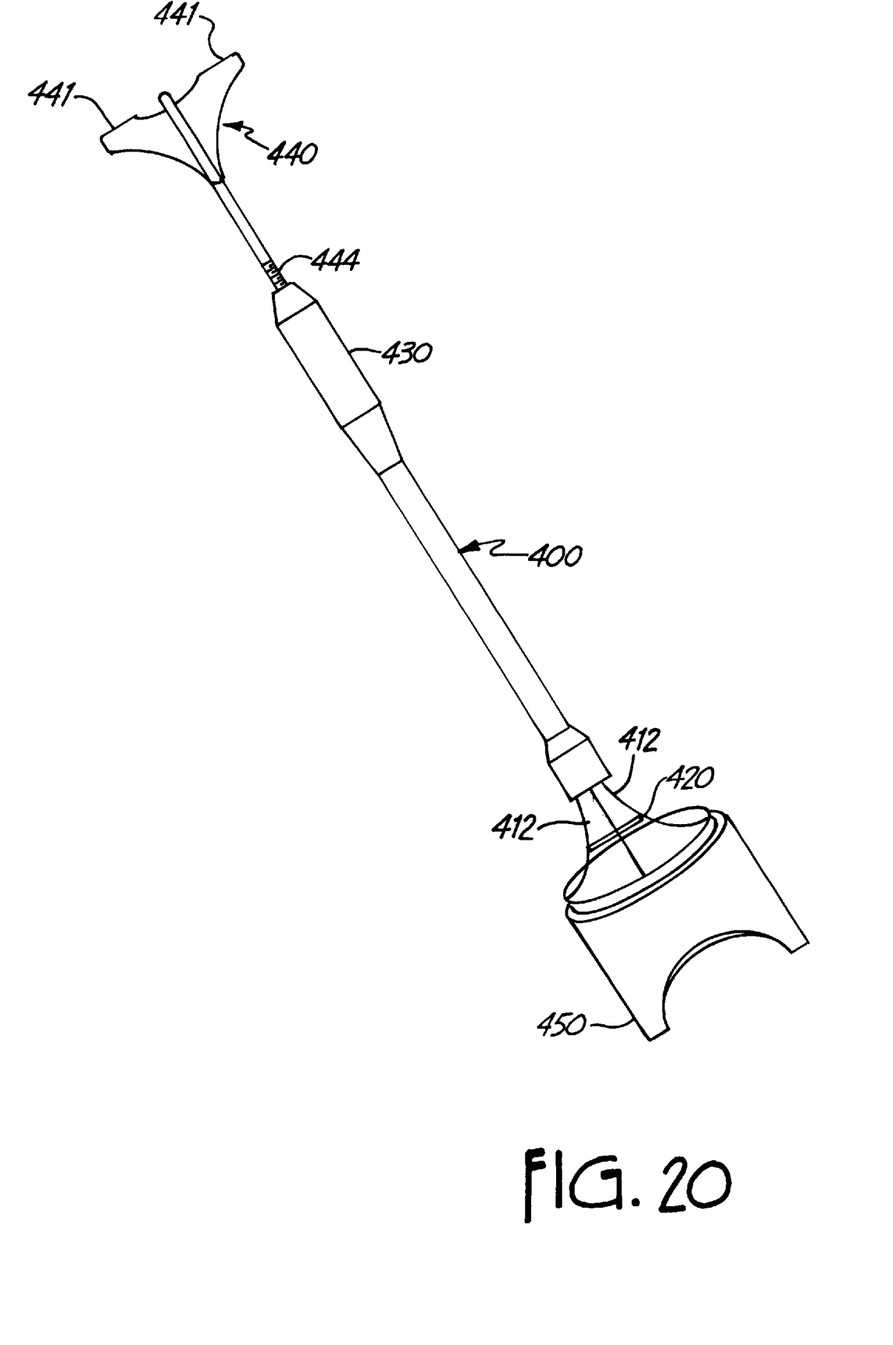
FIG. 20 is a perspective view of a universal stentless valve holder of the valve assembly kit of the present invention with the tissue heart valve attached.

The main objective of the universal stentless valve holder 400 is to facilitate the implantation of the tissue heart valve and shorten the surgical intervention time. The stentless valve holder 400 allows proper manipulation and apposition of the biologic heart valve surface with that of the mitral atrioventricular ring. The stentless valve holder 400 was designed to quickly hold and/or release any of the five tissue heart valve sizes available with valve assembly kit 10 of the present invention. As shown in FIG. 20, the stentless valve holder 400 provides a safe grip on the biologic heart valve 450, without placing undue strain on the tissue, and an unobstructed visual field to suture the tissue heart valve 450 around the mitral atrioventricular orifice.

Figure 21:
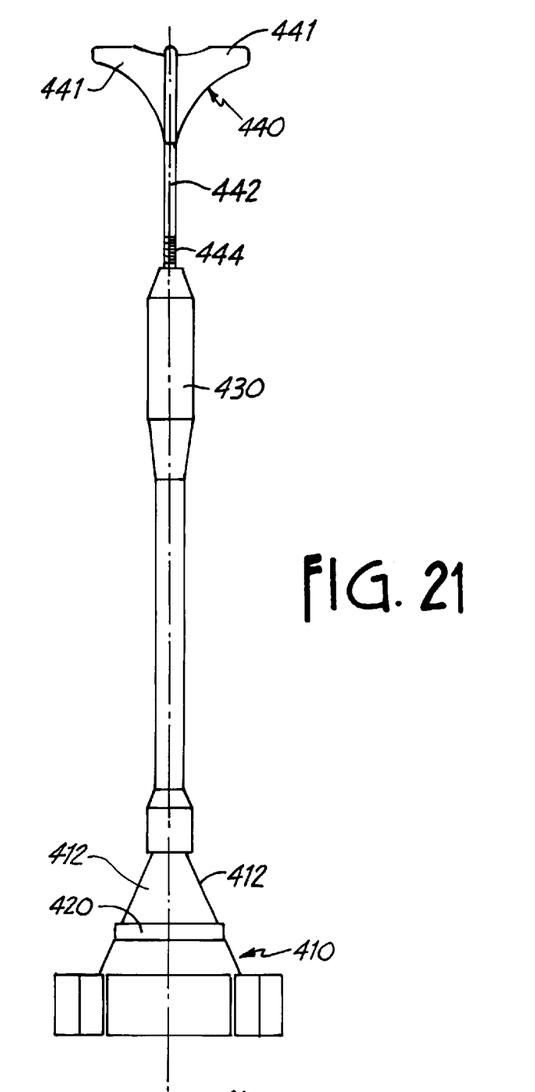
FIG. 21 is a side view of a universal stentless valve holder of the valve assembly kit of the present invention.
Figure 22:
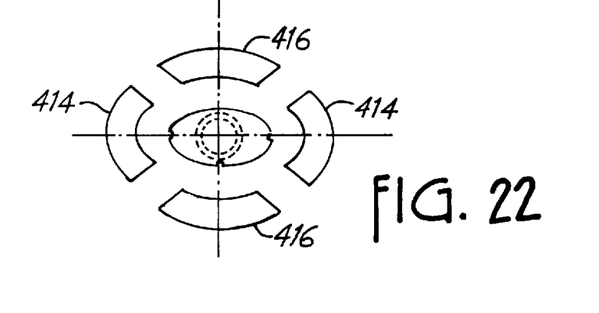
FIG. 22 is a bottom view of a universal stentless valve holder of the valve assembly kit of the present invention.

As shown in FIGS. 21 and 22, the universal stentless valve holder 400 comprises two principal segments: a main body 410 and a main handle 430 extending from the main body 410. The main body 410 performs the function of the stentless valve holder 400, i.e., supports the heart valve 450. The main body 410 is composed of a plurality of terminal arms 412 that are connected together at one extremity, and autonomous at a free end. At the free end, each terminal arm 412 has a supporting unit 414, 416 that will provide at least four support points to the base of stentless biologic valve. The terminal arms 412 are made out of an elastic steel rod having a preferred length of approximately 23 mm and a preferred diameter between 0.50 mm–1.00 mm. In a preferred embodiment of the present invention, the main body 410 consists of four terminal arms 412. In alternative embodiments of the present invention, additional terminal arms 412 are present.

The four diametrically opposed terminal arms 412 with their supporting units 414, 416 arranged in such a way that, when they are brought apart, form an ellipse along their perimeter. The circumference of the ellipse, formed by the outer surface of the support units 414, 416 can be modified to correspond with the circumference of a specific tissue heart valve. The terminal arms 412 are brought as far apart as necessary to suit the specific size of the tissue heart valve in use.

The support units 414, 416 are designed to come in close contact with the inner surface of the valve and hold the valve in place, as long as the four terminal arms 412 are extended. The supporting units 414, 416 have an external surface that comes in contact with the biological valve, and an internal surface that makes the connection with the terminal arm 412. The outer surface of the support units 414, 416 is made out of a material designed to prevent the sliding of the biologic tissue, and has preferred dimensions for the support unit 414 of 22 mm by 5 mm by 10 mm, and has preferred dimensions for the support unit 416 of 16 mm by 5 mm by 10 mm. In an alternative embodiment of the present invention, dacron felt is attached on the outer surface of the support units 414, 416 to increase the adhesion between the pericardial tissue and the support units 414, 416.

The four support units 414, 416 have the same dimensions and external surface area, the only difference is the radius of curvature of the circle segment. There are two pairs of diametrically opposed support units 414, 416, each pair having the same radius of curvature. The main body 410 in the extremity opposite to the supporting units 414, 416 is connected with the main handle 430. The valve holder 400 will fit at least the five tissue heart valves dimensions ranging from a smallest circumference of 90 mm to a largest circumference of 110 mm provided with the valve assembly kit 10 of the present invention.

The relative position of the terminal arms 412 can be modified by moving an ellipsoidal disc unit 420, located at the base of the terminal arms 412. The disc unit 420 has a close contact with the inner surface of the four terminal arms 412, and any modification in the position of the disc unit 420 will be followed by a change in the position of the terminal arms 412. For example, moving the disc unit 420 upward, the four terminal arms 412 will move symmetrically away from each other, and the perimeter of the ellipse delineated by the outer surface of the four supporting units 414, 416 will increase. The ellipsoidal disc unit 420 has the preferred dimensions of long axis 19 mm, short axis 10 mm, and a thickness of 2.5–3 mm.

The disc unit 420 is connected and operated by a rotating device 440 located at a free end of the main handle 430. The rotating device 440 and the disc unit4 20 are interconnected with a rigid cylindrical rod 442 that provides a simultaneous movement, as a single unit. The cylindrical rod 442 that connects the two components has preferred dimensions of 129 mm in length and 2 mm in diameter and is contained and coaxially aligned in the main handle 430. At the upper end the cylindrical rod 442 has a threaded segment 444. At the lower end, the cylindrical rod 442 is connected with the disc unit 420 in a modality that permits the cylindrical rod 442 to rotate freely at the joining point, while the disc unit 420 is in a fixed position. At the upper extremity the cylindrical rod 442 is connected with the rotating unit 440. By generating a circular motion with the rotating unit 440, the cylindrical rod 442 will displace the disc unit 420 up and down along the longitudinal axis of the valve holder 400. This mechanism is controlled by the threaded segment 444 of the cylindrical rod 442 that comes in close contact with the threaded interior portion of the main handle 430. The threaded segment 444 of the cylindrical rod 442 has a preferred length of approximately 13.5 mm, and the corresponding thread on the threaded interior portion of the handle 430 has a preferred length of approximately 35 mm.

The rotating unit 440 is the segment that will be manipulated by the surgeon in order to increase or decrease the circumference of the valve holder 400. The rotating unit 440 has four identical pallets 441 perpendicular to each other. The pallets 441 have the preferred dimensions of 16.40 mm by 15 mm by 2 mm.

The main handle 430 has a cylindrical shape, that is connected with the body of the valve holder 400 at one extremity and to the threaded segment 444 of the cylindrical rod 442 at the other extremity. The inner part of the main handle 430 contains the connecting rod 442 and the mechanical system necessary for the function of the valve holder 400. The main handle 430 has a preferred inner diameter of 3 mm and a preferred outer diameter of 5 mm. At the lower end of the main handle 430 the preferred outer diameter increases to 8 mm and the preferred inner diameter to 6 mm, in order to allow the attachment of the four terminal arms 412. The universal valve holder 400 is made of a combination of biocompatible plastic and elastic steel rods. The only components that will be made out of elastic steel rod are the four terminal arms 412 of the main body 410 of the valve holder 400. The preferred length of the universal valve holder 400 is approximately 160 mm.

Although the present invention has been described with reference to preferred embodiments, workers skilled in the art will recognize that changes may be made in form and detail without departing from the spirit and scope of the invention.

What is claimed is:

1. A valve assembly kit for forming a stentless autologous cardiac valve from membranes of pericardium tissue, the valve assembly kit comprising:

a valve assembly tray having a plane rectangular surface and a grooved channel extending from the plane rectangular surface to drain any fluids during formation of the stentless cardiac valve;

plurality of varying sized obturators that connect to a removable, universal handle, each varying sized obturator corresponding to an anatomical configuration a different mitral annulus for formation of varying sized stentless cardiac valves;

a tissue cutting device having a base unit with an inclined surface along an edge to facilitate the manipulation of the pericardium tissue, a guiding frame, and a cutting block; and a universal stentless valve holder configured to receive each of the varying sized obturators.

2. The kit of claim 1 wherein the valve assembly tray further comprises a plurality of basins a plurality of solution bottle stands and a plurality of handles.

3. The kit of claim 2 wherein each basin of the valve assembly tray is contoured to be large enough to permit the manipulation of a tissue fragment with an atraumatic forcep.

4. The valve assembly tray of claim 3 wherein each basin has a volume between 200 ml and 400 ml.

5. The kit of claim 2 wherein the plurality of solution bottle stands of the valve assembly tray permit the storage of a plurality of solution bottles and are cylindrical depressions in the valve assembly tray having an outer diameter slightly greater than an outer diameter of one of the plurality of solution bottles.

6. The kit of claim 2 wherein the plurality of handles extend from the plane rectangular surface to an outer surface of the plurality of basins.

7. The kit of claim 1 wherein the plane rectangular surface is used for mechanical manipulation of a tissue fragment during the formation of the stentless cardiac valve.

8. The plane rectangular surface of claim 1 wherein the grooved channel is trapezoidal in shape and located along a perimeter edge of the plane rectangular surface.

9. The kit of claim 1 wherein the plurality of obturators each have the same length and an elliptical transverse cross section that corresponds to an anatomical configuration of a mitral annulus.

10. The kit of claim 1 wherein the tissue cutting device includes a sharpened cutting blade perpendicular to a horizontal surface of a cutting block.

11. The kit of claim 10 wherein the cutting blade is contoured to a shape of a tissue fragment necessary to form a specific cardiac valve size.

12. The kit of claim 1 wherein the universal stentless valve holder has a plurality of terminal arms that support an assembled cardiac valve and can be manipulated for implantation of the cardiac valve.

13. A surgical kit for use in an operating room to assist in a stentless cardiac valve replacement procedure, the surgical kit comprising:

a tissue cutting device having a base unit with an inclined surface along an edge to facilitate the manipulation of the pericardium tissue, a guiding frame, a cutting block, and cutting means to form a specific stentless cardiac valve size; and plurality of varying sized obturators that connect to a removable, universal handle, each varying sized obturator corresponding to an anatomical configuration a different mitral annulus for formation of varying sized stentless cardiac valves.

14. The surgical kit of claim 13 further comprising a valve assembly tray having a plurality of basins, a plane rectangular surface, a plurality of solution bottle stands and a plurality of handles.

15. The surgical kit of claim 14 wherein each basin of the valve assembly tray is contoured to be large enough to permit the manipulation of the tissue fragment with an atraumatic forcep.

16. The valve assembly tray of claim 15 wherein each basin has a volume between 200 ml and 400 ml.

17. The surgical kit of claim 14 wherein the plurality of solution bottle stands of the valve assembly tray permit the storage of a plurality of solution bottles and are cylindrical depressions in valve assembly tray having an outer diameter slightly greater than an outer diameter of one of the plurality of solution bottles.

18. The surgical kit of claim 14 wherein the plane rectangular surface of the valve assembly tray is used for mechanical manipulation of the tissue fragment during the formation of the cardiac valve and contains a grooved channel to drain any fluids present during the manipulation.

19. The plane rectangular surface of claim 18 wherein the grooved channel is trapezoidal in shape and located along a perimeter edge of the plane rectangular surface.

20. The kit of claim 14 the plurality of handles extend from the plane rectangular surface to an outer surface of the plurality of basins.

21. The surgical kit of claim 13 further comprising a universal stentless valve holder configured to receive each of the varying sized obturators and having a plurality of terminal arms that support the cardiac valve and can be manipulated for implantation of the cardiac valve.

22. The surgical kit of claim 13 wherein the cutting means of the tissue cutting device is a cutting blade contoured to a shape of a tissue fragment necessary to form a specific cardiac valve size.

23. The surgical kit of claim 22 wherein the cutting blade is sharpened and perpendicular to a horizontal surface of a cutting block.

24. A cardiac valve assembly kit for forming a stentless autologous cardiac valve from membranes of pericardium tissue, the cardiac valve assembly kit comprising:

a tissue cutting device having a base unit with an inclined surface along an edge to facilitate the manipulation of the pericardium tissue, a guiding frame, a cutting block, and a sharpened cutting blade contoured to a shape of a tissue fragment necessary to form a specific stentless cardiac valve size;

a plurality of varying sized obturators that connect to a removable universal handle, each obturator having an elliptical transverse cross section that corresponds to an anatomical configuration of a mitral annulus for formation of varying sized stentless cardiac valves;

a valve assembly tray having a plurality of basins contoured to be large enough to permit the manipulation of the tissue fragment with an atraumatic forcep, a plane rectangular surface having a grooved channel to drain any fluids present during manipulation of the cardiac valve, a plurality of solution bottle stands that permit the storage of a plurality of solution bottles and a plurality of handles; and a universal stentless valve holder configured to receive each of the varying sized obturators and having a plurality of terminal arms that support the stentless cardiac valve and can be manipulated for implantation of the stentless cardiac valve.

* * * * *

UNITED STATES PATENT AND TRADEMARK OFFICE
CERTIFICATE OF CORRECTION

PATENT NO. : 6,342,069 B1
DATED : January 29, 2002
INVENTOR(S) : Dan Deac et al.

It is certified that error appears in the above-identified patent and that said Letters Patent is hereby corrected as shown below:

Column 5,
Line 6, delete "10" after "of the"

Column 7,
Line 63, delete "a traumatic", insert -- atraumatic --

Column 10,
Line 49, before "plurality", insert -- a --

Column 11,
Line 38, before "plurality", insert -- a --

Column 12,
Line 1, after "in", insert -- the --

Signed and Sealed this

Eleventh Day of June, 2002

Attest:

JAMES E. ROGAN
Attesting Officer
Director of the United States Patent and Trademark Office